(12) United States Patent
Wright et al.

(10) Patent No.: US 7,527,058 B2
(45) Date of Patent: May 5, 2009

(54) RESPIRATORY SUCTION CATHETER ASSEMBLY

(75) Inventors: Clifford A. Wright, San Diego, CA (US); Robert F. Eisele, Carlsbad, CA (US)

(73) Assignee: Medical Device Group, Inc., Poway, CA (US)

( * ) Notice: Subject to any disclaimer, the term of this patent is extended or adjusted under 35 U.S.C. 154(b) by 182 days.

(21) Appl. No.: 11/424,200

(22) Filed: Jun. 14, 2006

(65) Prior Publication Data

US 2007/0293812 A1 Dec. 20, 2007

(51) Int. Cl.
*A61M 16/00* (2006.01)

(52) U.S. Cl. .............. 128/207.14; 128/200.28; 128/207.16

(58) Field of Classification Search .......... 128/200.26, 128/207.14, 912, 207.16
See application file for complete search history.

(56) References Cited

U.S. PATENT DOCUMENTS

| | | | |
|---|---|---|---|
| 4,227,529 A | 10/1980 | Lomholt | |
| 4,287,889 A | 9/1981 | Stupar | |
| 4,291,691 A | 9/1981 | Cabal et al. | |
| 4,300,550 A | 11/1981 | Gandi et al. | |
| 4,468,216 A | 8/1984 | Muto | |
| 4,569,344 A | 2/1986 | Palmer | |
| 4,638,539 A | 1/1987 | Palmer | |
| 4,648,871 A | 3/1987 | Jacob | |
| 4,662,871 A | 5/1987 | Rafelson | |
| 4,696,296 A | 9/1987 | Palmer | |
| 4,795,447 A | 1/1989 | Dodson | |
| 4,825,859 A | 5/1989 | Lambert | |
| 4,834,726 A | 5/1989 | Lambert | |
| 4,836,199 A | 6/1989 | Palmer | |
| 4,850,350 A | 7/1989 | Jackson | |
| 4,872,579 A | 10/1989 | Palmer | |
| 4,938,741 A | 7/1990 | Lambert | |
| 4,967,743 A | 11/1990 | Lambert | |
| 5,073,164 A | 12/1991 | Hollister et al. | |
| 5,083,561 A | 1/1992 | Russo | |
| 5,088,486 A | 2/1992 | Jinotti | |
| 5,101,817 A | 4/1992 | Etter | |
| 5,125,893 A | 6/1992 | Dryder | |
| 5,167,622 A | 12/1992 | Muto | |
| 5,188,592 A | 2/1993 | Hakki | |
| 5,220,916 A | 6/1993 | Russo | |
| 5,254,098 A | 10/1993 | Ulrich et al. | |
| 5,255,676 A | 10/1993 | Russo | |
| 5,269,768 A | 12/1993 | Cheung | |
| 5,300,043 A | 4/1994 | Devlin et al. | |
| 5,309,902 A | 5/1994 | Kee et al. | |

(Continued)

*Primary Examiner*—Steven O Douglas
(74) *Attorney, Agent, or Firm*—Perkins Coie LLP

(57) ABSTRACT

A closed suction catheter includes a valve assembly and a manifold. A catheter tube is attached to the valve assembly and slidably secured within the manifold. The closed suction catheter may include one or more features for promoting an effective, safe, and efficient process for suctioning mucus and other fluids from a patient's lungs, and for cleaning the various components of the catheter system. For example, the closed suction catheter may include a tube wiper having a reinforced leading ridge and/or an internal ledge for efficiently wiping the catheter tube. The valve assembly may include a locking mechanism having a slider unit, a cam arm, and/or ribs that engage openings in the slider unit for maintaining a valve stem in proper alignment and an actuator on the valve assembly in a locked position. The closed suction catheter may include several other features, as well.

22 Claims, 15 Drawing Sheets

U.S. PATENT DOCUMENTS

| | | |
|---|---|---|
| 5,325,850 A | 7/1994 | Ulrich et al. |
| 5,349,950 A | 9/1994 | Ulrich et al. |
| 5,379,549 A | 1/1995 | Carcich et al. |
| 5,431,637 A | 7/1995 | Okada et al. |
| 5,460,613 A | 10/1995 | Ulrich et al. |
| 5,490,503 A | 2/1996 | Hollister |
| 5,496,287 A | 3/1996 | Jinotti |
| 5,578,006 A | 11/1996 | Schon |
| 5,643,230 A | 7/1997 | Linder |
| 5,653,231 A | 8/1997 | Bell |
| 5,676,136 A | 10/1997 | Russo |
| 5,694,927 A | 12/1997 | Bohmfalk |
| 5,713,849 A | 2/1998 | Bosma et al. |
| 5,730,123 A | 3/1998 | Lorenzen et al. |
| 5,730,727 A | 3/1998 | Russo |
| 5,738,091 A | 4/1998 | Kee et al. |
| 5,779,687 A | 7/1998 | Bell et al. |
| 5,788,680 A | 8/1998 | Linder |
| 5,919,174 A * | 7/1999 | Hanson .................... 604/533 |
| 5,931,831 A | 8/1999 | Linder |
| 6,012,451 A | 1/2000 | Palmer |
| 6,227,200 B1 | 5/2001 | Crump et al. |
| 6,237,596 B1 | 5/2001 | Bohmfalk |
| 6,428,498 B2 | 8/2002 | Uflacker |
| 6,436,085 B1 | 8/2002 | Lauer |
| 6,494,203 B1 | 12/2002 | Palmer |
| 6,551,278 B1 | 4/2003 | Geitz |
| 6,588,425 B2 | 7/2003 | Rouns et al. |
| 6,588,427 B1 | 7/2003 | Carlsen et al. |
| 6,609,520 B1 | 8/2003 | Carlsen et al. |
| 6,769,430 B1 | 8/2004 | Carlsen et al. |
| 6,923,184 B1 | 8/2005 | Russo |
| 6,935,339 B2 | 8/2005 | Mattar Neto et al. |
| 7,263,997 B2 * | 9/2007 | Madsen et al. ......... 128/207.14 |

* cited by examiner

RESPIRATORY SUCTION CATHETER ASSEMBLY

BACKGROUND

Many medical situations arise in which a patient requires insertion of an endotracheal tube, or other artificial airway, into the patient's respiratory system. In some cases, the endotracheal tube must remain in the patient for an extended duration, such as when a patient is hooked up to a ventilation machine, or "ventilator," that provides oxygen to the patient. In these cases, it is necessary to periodically remove respiratory fluids, such as mucus and other secretions, from the patient's respiratory system.

Suction catheters, which are inserted into the artificial airway, have long been used to remove these respiratory secretions. When withdrawn, a negative pressure applied to the interior of the suction catheter draws secretions out of the patient's respiratory system. Traditional suction catheters required the patient to be temporarily disconnected from the ventilator during the suctioning process, which would cut off the patient's air flow and often lead to patient panic or distress.

Closed suction catheters were developed to overcome this problem. A closed suction catheter is typically maintained within a protective cover or sheath to protect medical technicians and others from exposure to infectious agents that might end up on the outside of the catheter tube. One advantage of using a closed suction catheter is that the patient does not need to be disconnected from the ventilator during the suctioning process. Indeed, the catheter tube is guided through a manifold, to which the ventilator and the catheter are attached, into the artificial airway while the ventilator continues to provide oxygen to the patient.

Closed suction catheters are typically used multiple times for suctioning in a given day. Accordingly, it is important to remove secretions from the catheter tube between uses in order to reduce the risk of contamination. While existing closed suction catheters typically include components for cleaning the catheter tube, they are often inefficient and do not always achieve desired cleanliness standards. Existing closed suction catheter systems often have other shortcomings, as well, such as leaky or unstable valves and components that restrict patient movement. Thus, a need exists for an improved closed suction catheter system.

SUMMARY

A closed suction catheter includes a valve assembly and a manifold. A catheter tube is attached to the valve assembly and slidably secured within the manifold. The closed suction catheter includes one or more features for promoting an effective, safe, and efficient process for suctioning mucus and other fluids from a patient's lungs, and for cleaning the various components of the catheter system. The closed suction catheter may, for example, include a tube wiper having a reinforced leading ridge and/or an internal ledge for efficiently wiping the catheter tube. The valve assembly of the catheter may include a locking mechanism having a slider unit, a cam arm, and/or ribs that engage openings in the slider unit for maintaining a valve stem in proper alignment and an actuator on the valve assembly in a locked position.

Several other features and advantages of the invention will appear hereinafter. The features of the invention described above can be used separately or together, or in various combinations of one or more of them. The invention resides as well in sub-combinations of the features described. Furthermore, many of the method steps described herein may be performed in a different order than that which is explicitly described.

BRIEF DESCRIPTION OF THE DRAWINGS

In the drawings, wherein the same reference number indicates the same element throughout the several views.

DETAILED DESCRIPTION

Various embodiments of the invention will now be described. The following description provides specific details for a thorough understanding and enabling description of these embodiments. One skilled in the art will understand, however, that the invention may be practiced without many of these details. Additionally, some well-known structures or functions may not be shown or described in detail so as to avoid unnecessarily obscuring the relevant description of the various embodiments.

Figure 1:
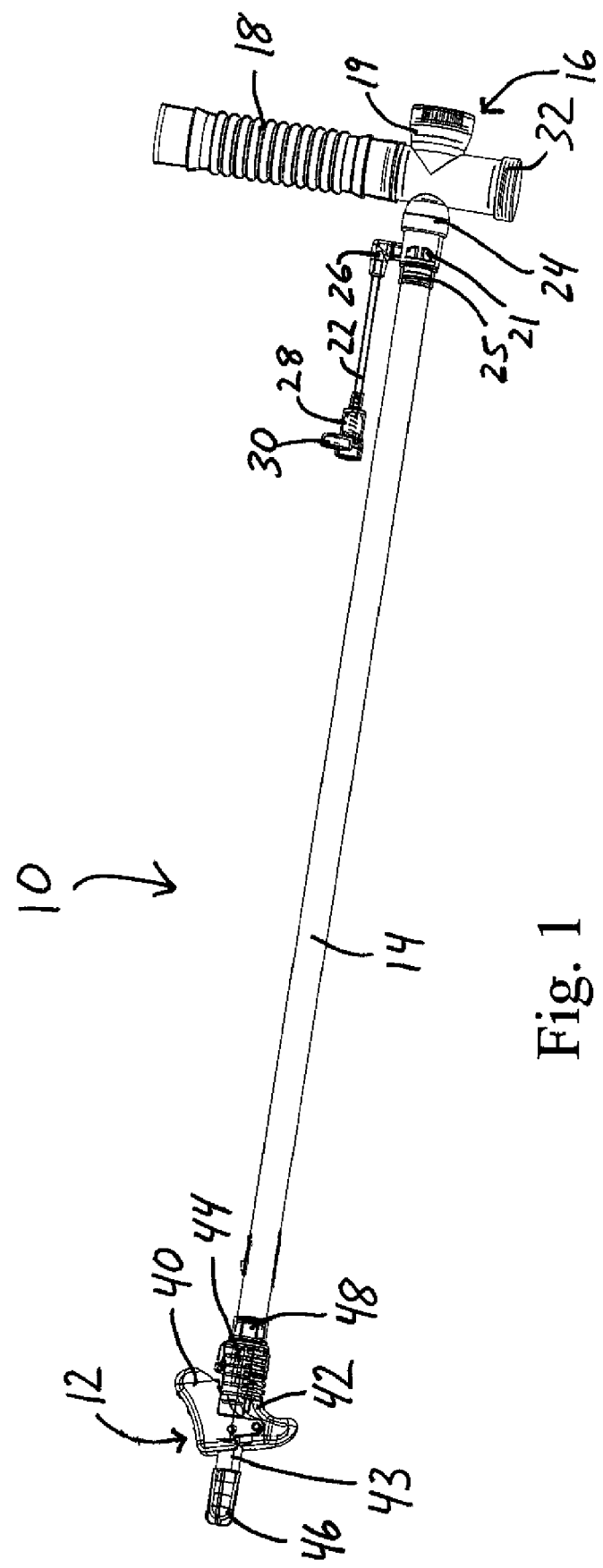
FIG. 1 is a perspective view of a closed suction catheter according to one embodiment.
Figure 2:
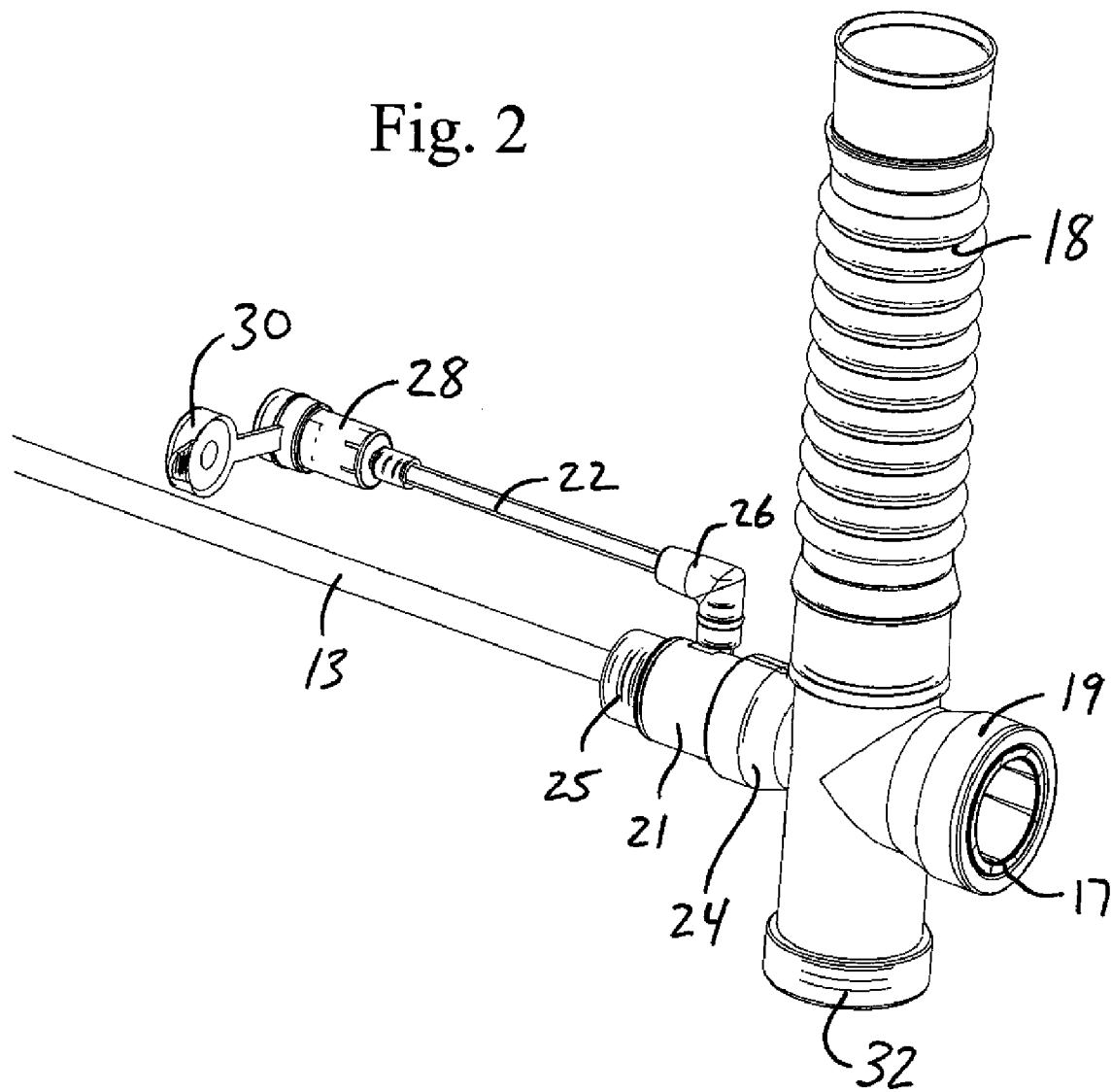
FIG. 2 is a side-perspective view of the T-piece assembly, lavage housing, flexible tube, and catheter tube of the closed suction catheter shown in FIG. 1.
Figure 3:
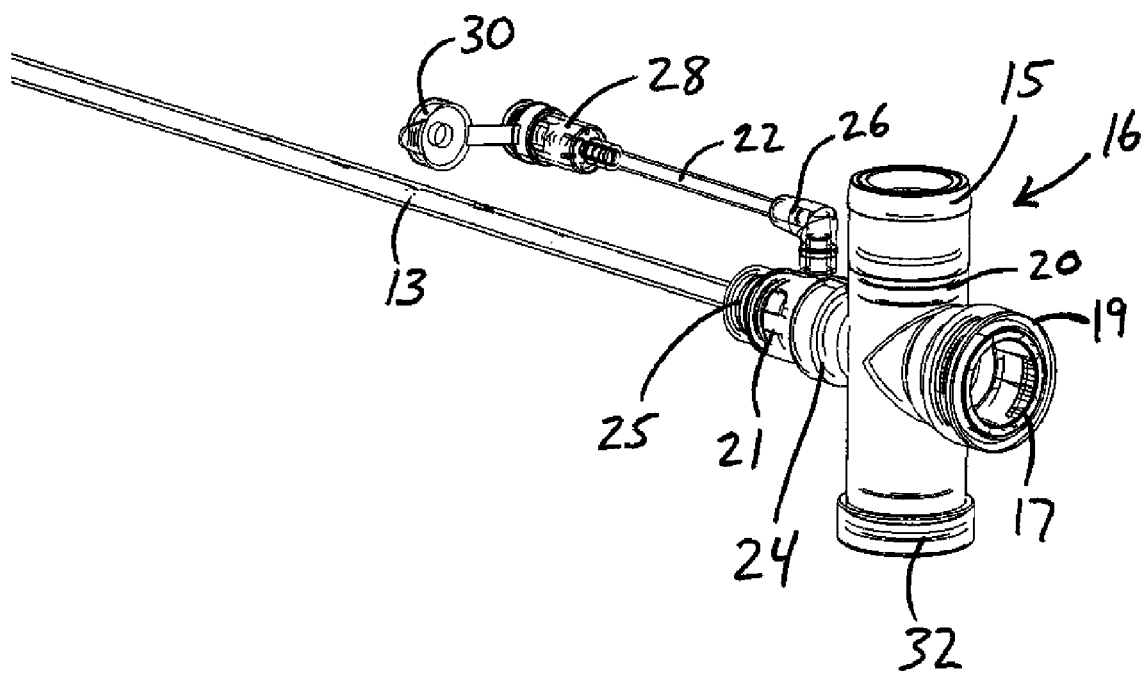
FIG. 3 is a side-perspective view of the T-piece assembly and catheter tube shown in FIG. 2.
Figure 11:
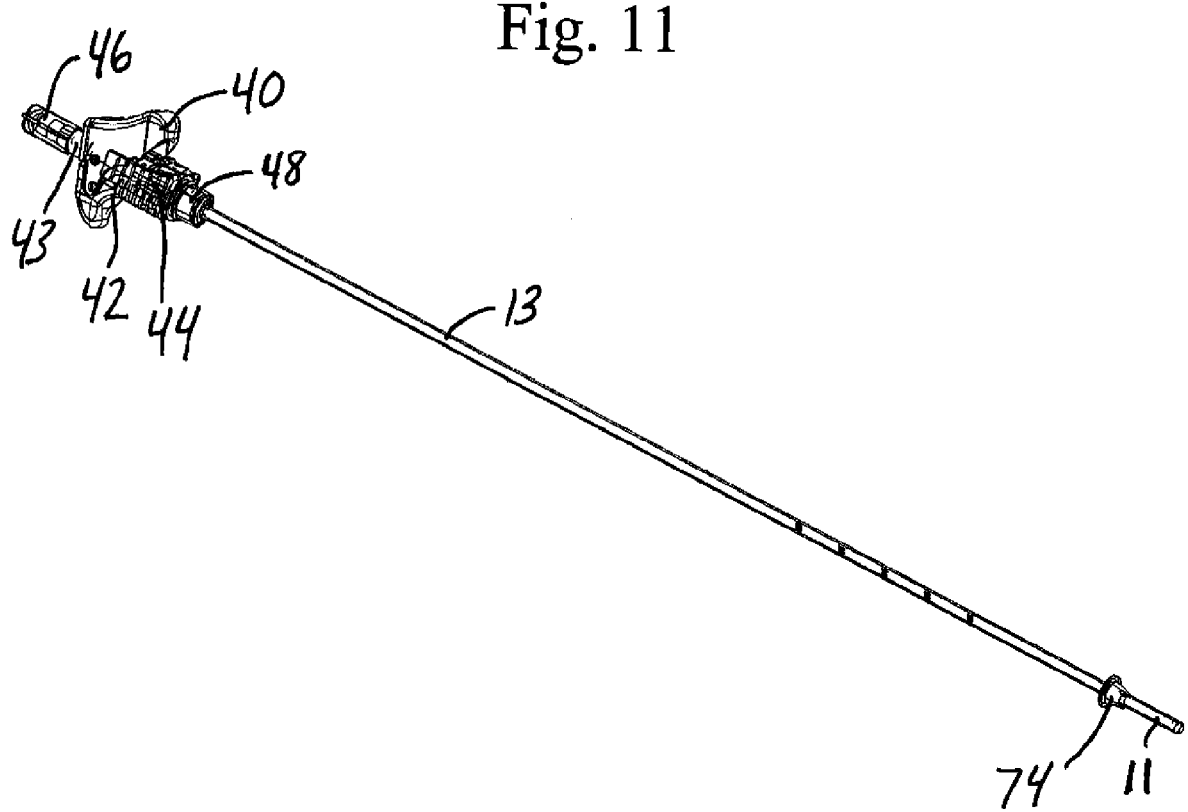
FIG. 11 is a perspective view of the valve assembly, catheter tube, and tube-wiper of the closed suction catheter shown in FIG. 1.
Figure 12:
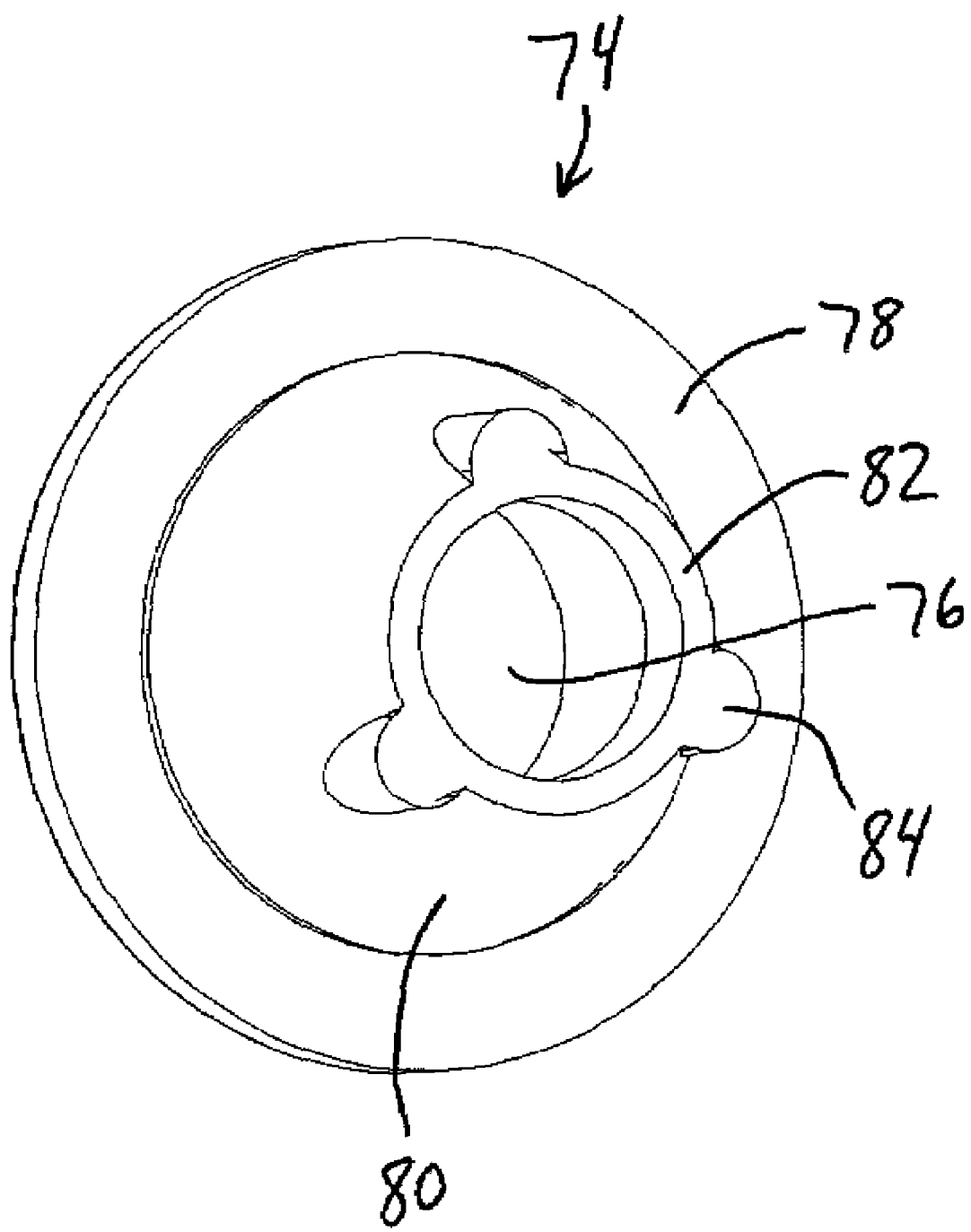
FIG. 12 is a front-perspective view of the tube-wiper shown in FIG. 11.

The terminology used in the description presented below is intended to be interpreted in its broadest reasonable manner, even though it is being used in conjunction with a detailed description of certain specific embodiments of the invention. Certain terms may even be emphasized below. Any terminology intended to be interpreted in any restricted manner, however, will be overtly and specifically defined as such in this detailed description section.

Where the context permits, singular or plural terms may also include the plural or singular term, respectively. Moreover, unless the word "or" is expressly limited to mean only a single item exclusive from the other items in a list of two or more items, then the use of "or" in such a list is to be inter- FIG. 1 illustrates a closed suction catheter 10, according to one embodiment. In the remaining drawings, several elements shown in FIG. 1 are omitted for clarity so that specific elements of the closed suction catheter 10 can be better shown and described. The closed suction catheter 10 includes a valve assembly 12 attached to a first end of a catheter tube 13 (visible in FIGS. 2, 3, and 11, for example). The catheter tube 13 is contained within a sheath 14 or sleeve. The sheath 14 may be made of a thin, plastic, pliable material or other suitable material. The other end of the catheter tube 13 is slidably secured within a manifold 16.

Figure 4:
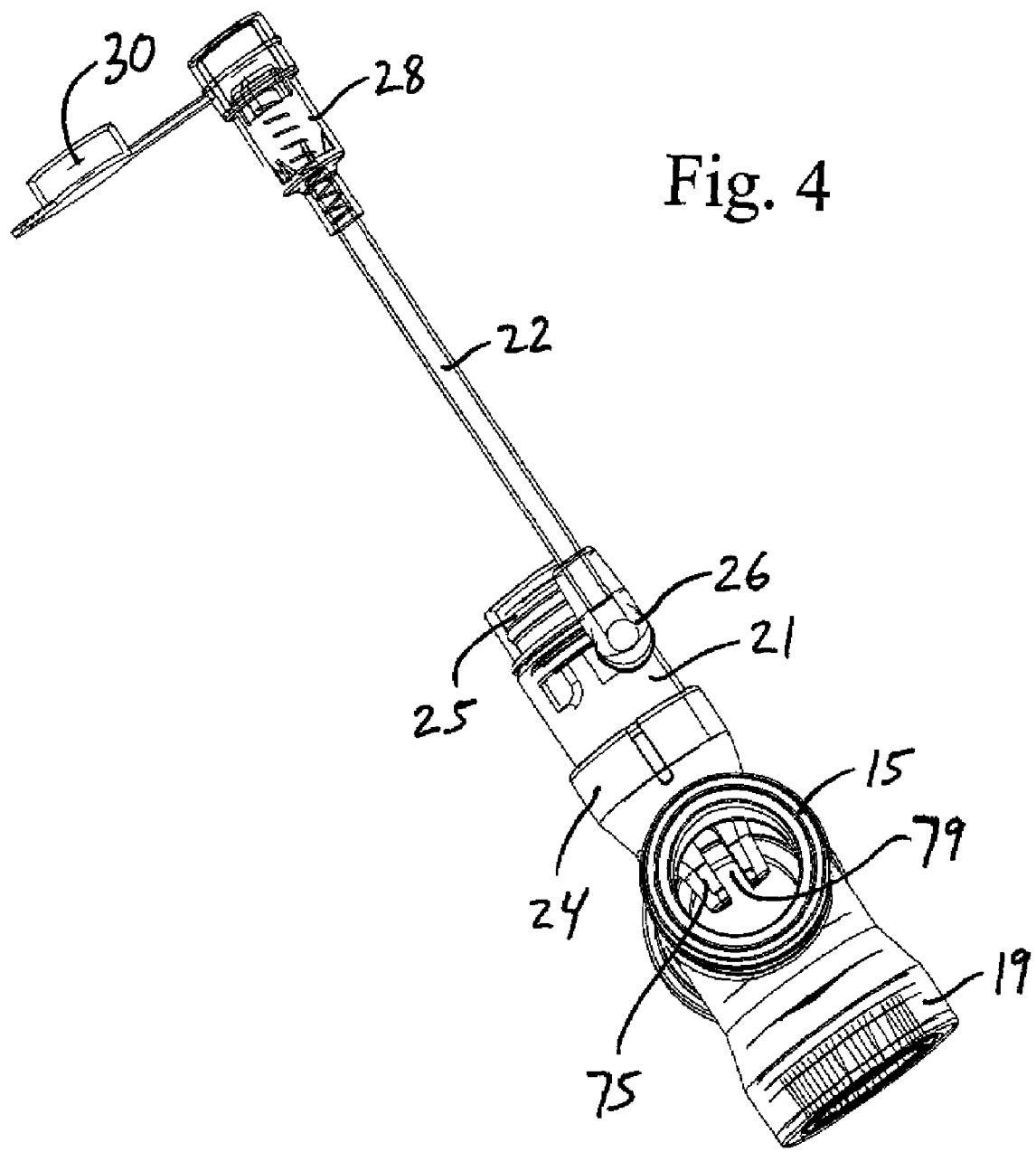
FIG. 4 is a top-perspective view of the T-piece assembly shown in FIGS. 2 and 3.

A corrugated or flexible tube 18, which is configured to be coupled or connected to a ventilator hose or tube, is optionally connected to an upper arm 20 of the manifold 16. The flexible tube 18 may be rotatably connected to the manifold 16 via an inner or outer rotatable sleeve 15 (visible in FIGS. 3 and 4) on the upper arm 20 of the manifold 16. The manifold 16 also includes an outer arm 19, which optionally includes an outer or inner rotatable sleeve 17 (visible in FIGS. 2 and 3) for connection to a coupling or other connector on an endotracheal tube or other artificial airway. The rotatable sleeves 15, 17 may be attached to the manifold 16 via a snap-fit (e.g., a groove that snaps over a ridge) or a lock-fit, or via any other suitable connection. By providing these rotatable connections, the catheter 10 is able to rotate when a patient moves, allowing the patient relative freedom of movement without hindrance from the catheter 10.

A lavage housing 21 is connected to an inner arm 24 of the manifold 16. A first snap-ring or sheath retainer 25 is connected to an inner portion of the lavage housing 21. The sheath 14 is secured between the first sheath retainer 25 and an inwardly extending portion of the lavage housing 21 positioned within the first sheath retainer 25. A lavage tube 22 is connected to, and in fluid communication with, an upper portion of the lavage housing 21 via an elbow joint 26 or other suitable connector. A valve housing 28 containing a poppet valve 29 (visible in FIG. 15) or similar element is attached to the other end of the lavage tube 22. The valve housing 28 optionally includes a valve cap 30 for closing off the opening to the poppet valve 29 when it is not in use. A lower arm of the manifold 16 includes a removable manifold cap 32 for closing off a lower opening in the manifold 16.

Figure 15:
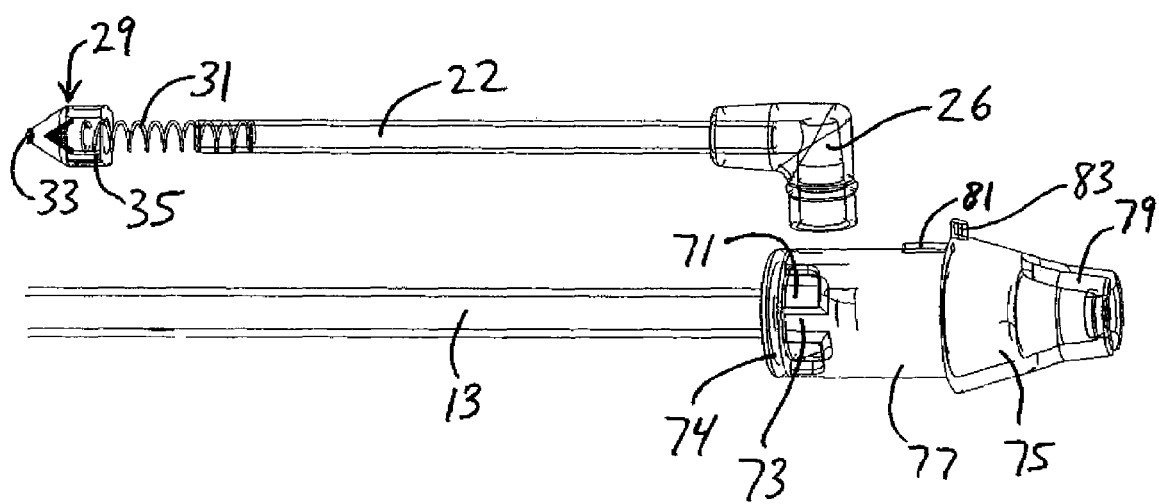
FIG. 15 is a side-perspective view of the catheter tube and components of the lavage mechanism (with the lavage housing removed for clarity) shown in FIG. 1.

As shown in FIG. 15 (in which the valve housing 28 and the lavage housing 21 are omitted for clarity), the poppet valve 29 is preferably loaded with a spring 31 and includes a tip 33 with an opening. Saline, water, or other fluids for cleaning the catheter tube 13 and other system components may be injected into the system, via a syringe or similar device, through the opening in the tip 33 of the poppet valve 29. The poppet valve 29 preferably includes multiple outer ridges 35 that form fluid flow paths around the outer surface of the poppet valve 29. As a result, if the opening in the tip 33 of the poppet valve is unintentionally occluded by a syringe, which is a relatively common occurrence, fluid injected into the valve body 28 is able to travel around the exterior of the poppet valve 29 and into the lavage tube 22.

Figure 5:
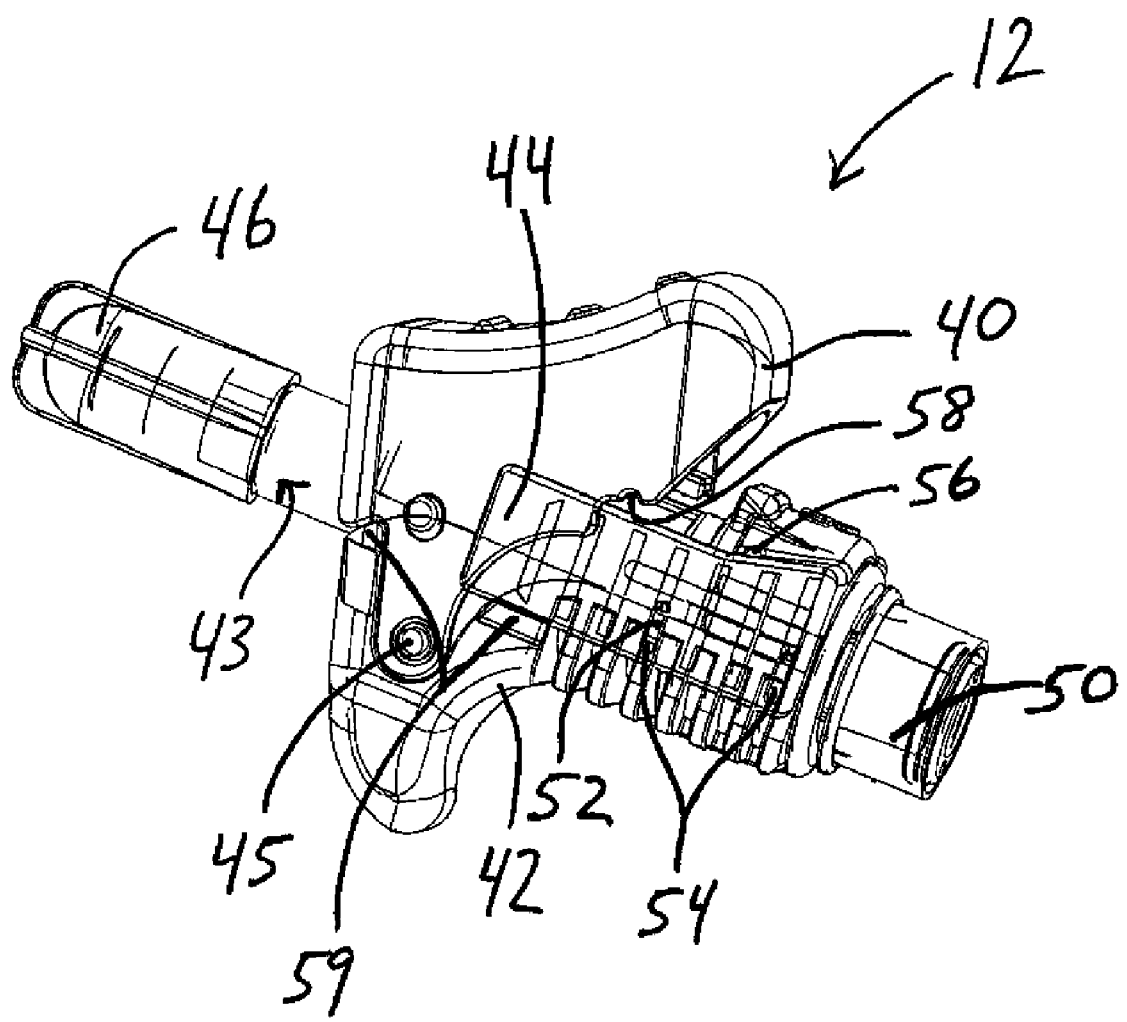
FIG. 5 is a side-perspective view of the valve assembly of the closed suction catheter shown in FIG. 1.
Figure 6:
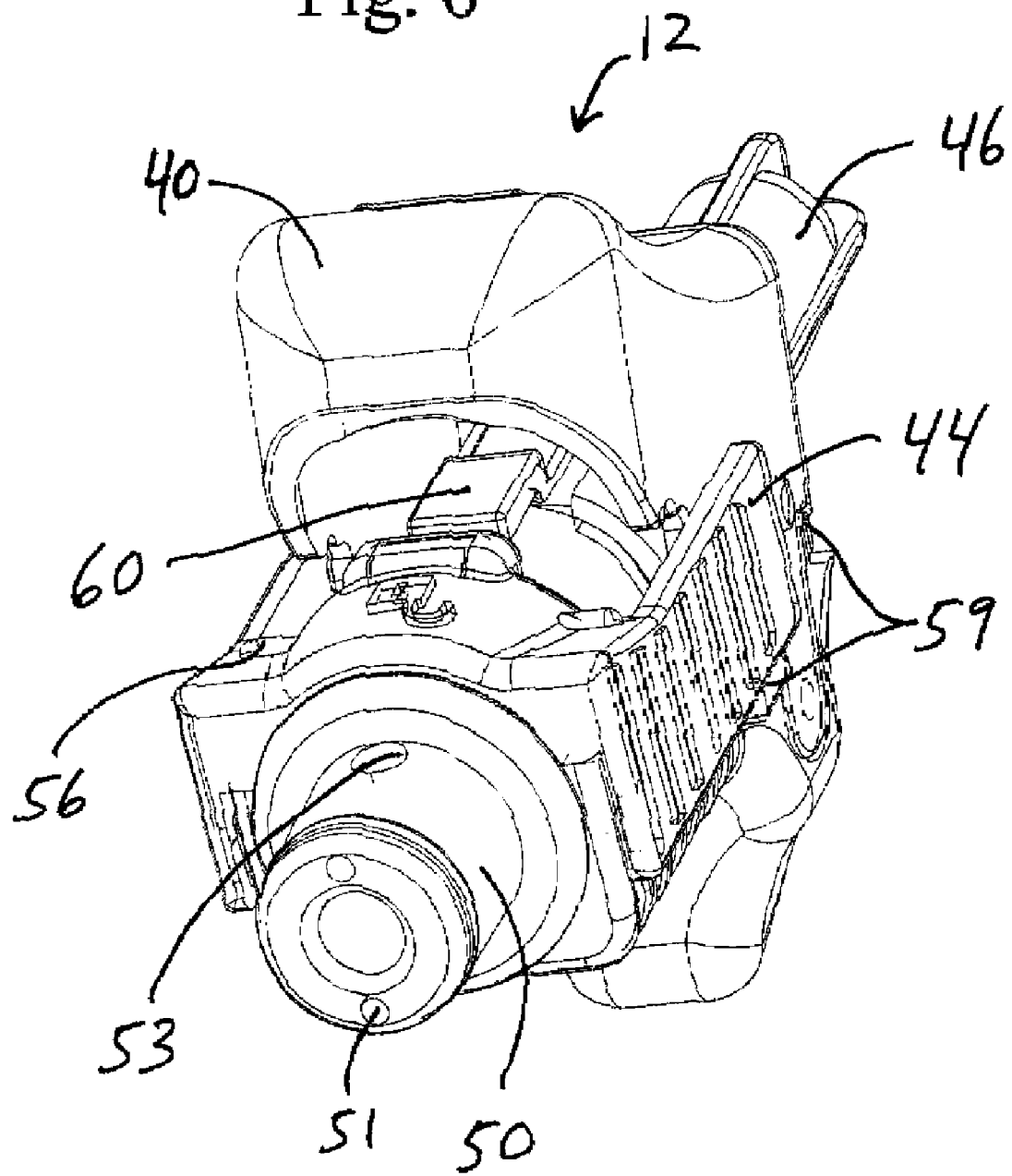
FIG. 6 is a front-perspective view of the valve assembly shown in FIG. 5.
Figure 7:
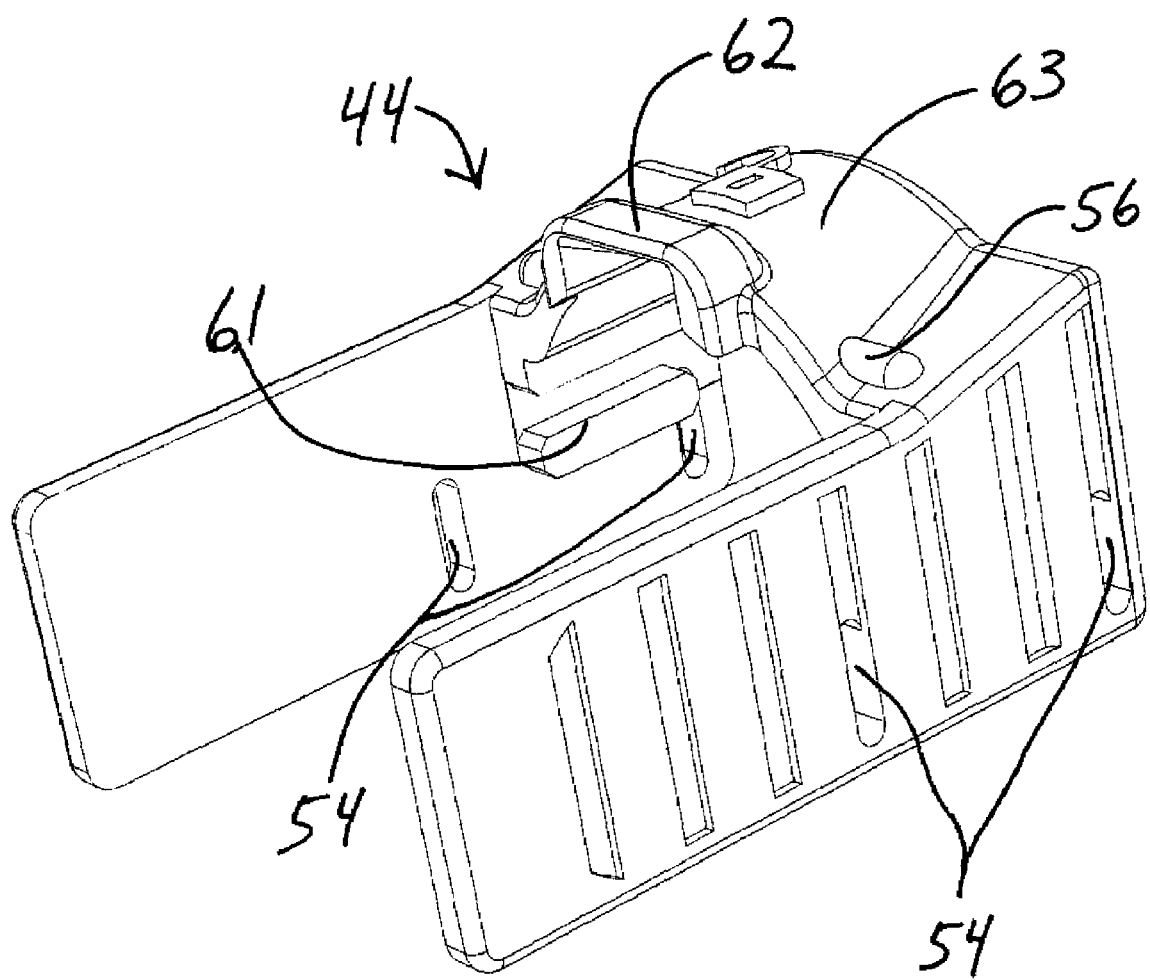
FIG. 7 is a perspective view of slider unit of the valve assembly shown in FIGS. 5 and 6.
Figure 8:
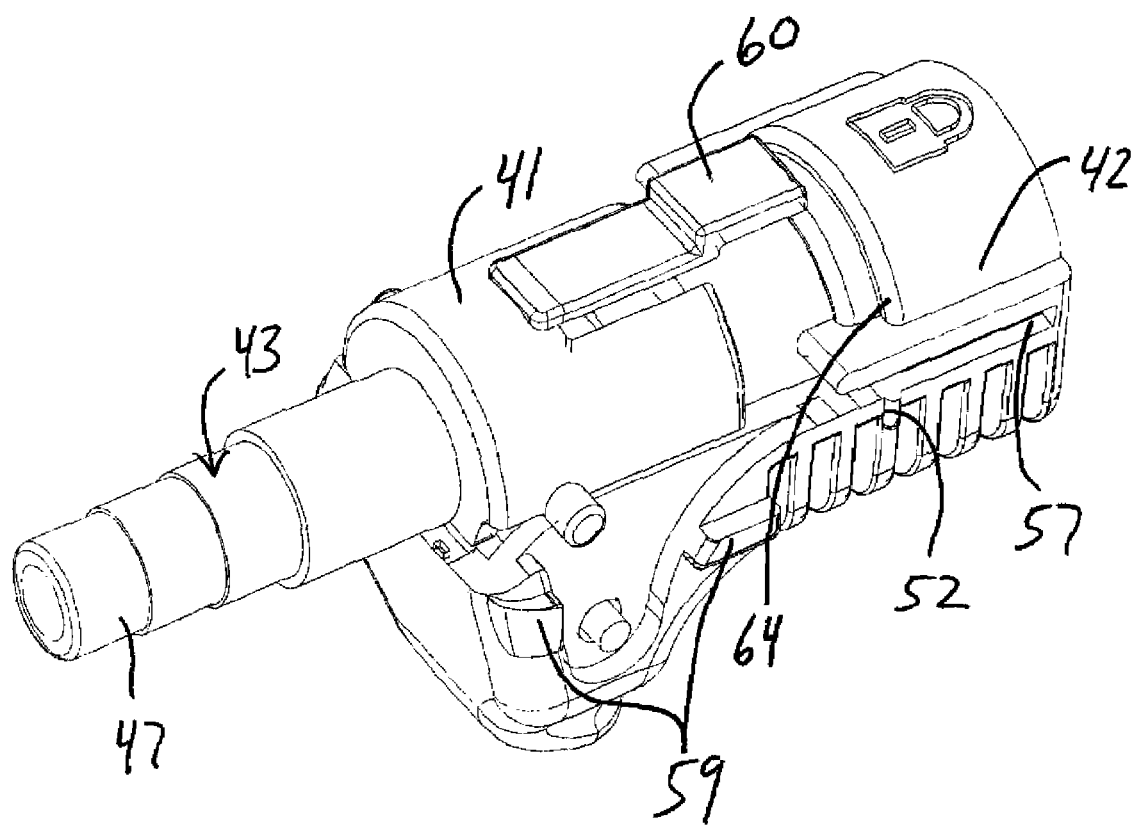
FIG. 8 is a perspective view of the valve stem, valve body, and cam arm components of the valve assembly shown in FIGS. 5-7.

Referring to FIGS. 5-10, the valve assembly 12 includes a button 40 or other actuator pivotally attached to a valve body 42 via a pin 45 or other suitable connector. The button 40 is biased into an "up" position (as shown in FIGS. 5 and 6) via a spring-loaded retainer 41 or other suitable biasing mechanism. A valve stem 43, which may be disposed within the spring of the retainer 41, is attached to an underside of the retainer 41. A barb cap 46 may be included on a barb portion 47 of the valve stem 43 for covering the barb portion 47 when it is not in use, i.e., when it is not connected to suction tubing associated with a vacuum system or other suction system.

By including the barb portion 47 directly on the valve stem 43, the barb portion 47 moves in unison with the valve stem 43 when the button 40 is pressed, and the number of components required to make up the valve assembly 12 is reduced. Furthermore, the efficiency of the suctioning process is increased, since components commonly used in systems where the hose barb is separate from the valve stem, such as a suction plunger valve, are not required. Thus, there is less "dead" vacuum or suction space, and a constant flow of suctioning air is provided between the valve stem 43 and the barb portion 47.

An intake 50 (visible in FIGS. 5 and 6) is positioned on the catheter tube 13 within a second snap-ring or sheath retainer 48 (not shown in FIGS. 5 and 6, for clarity) on the valve assembly 12. The sheath 14 is secured between the second sheath retainer 48 and the intake 50. The intake 50 is preferably a one-piece component that includes one or more outlets for releasing air that inadvertently fills up the sheath 14. In one embodiment, the intake 50 includes one or more outlet ports 51 through which air may exit the interior of the sheath 14, and one or more exit ports 53, in fluid communication with the outlet ports 51, through which the air may exit the intake 50 and the system. The one or more exit ports 53 are preferably oriented at approximately 90° relative to the outlet ports 51 so that air exits in a direction away from the patient. The one or more exit ports 53 are optionally larger than the outlet ports 51 so that the velocity of the exiting air increases as it travels through the intake 50.

Pressing down on the button 40 actuates the retainer 41 and moves the valve stem 43 toward the catheter tube 13 (from left to right in FIG. 5), which opens the valve and provides a suctioning force through the catheter tube 13 when the barb portion 47 of the valve stem 43 is connected to a vacuum system or other suction system (via suction tubing or a similar connector). The catheter tube 13 includes one or more eyeholes or openings 11 (visible in FIG. 11), in or near the tip at the free end of the catheter tube 13, through which fluid may be suctioned into the catheter tube 13. This suctioning action is used to remove mucus and other fluids from the lungs of a patient, or to remove from the system fluid that settles in the manifold 16 (by rotating the manifold 16 to allow the fluid to flow toward the lavage housing 21 so that it can be suctioned through the catheter tube 13). It is important to remove any stagnant fluid from the manifold 16 because such fluid can become bacterial, and can also produce irritating slushing noises and trigger audible low pressure alarms associated with the ventilator.

The valve assembly 12 further includes a locking mechanism for maintaining the button 40 in the "up" or locked position when the valve assembly 12 is not in use. The locking mechanism includes a slider unit 44 slidably or otherwise movably secured to the valve body 42. The slider unit 44 includes internal guide rails 61 for engaging corresponding external channels 57 on the valve body 42. This configuration promotes smooth sliding movement of the slider unit 44 while maintaining it in a level, properly aligned position.

The valve body preferably includes one or more outwardly projecting steps or ribs 52 for engagement with one or more corresponding openings 54 on the slider unit 44. In the embodiment shown, each side of the valve body 42 includes one rib 52 for separately engaging one of two openings 54 (which correspond to unlocked and locked positions) present on each side of the slider unit 44. In the illustrated position, a rib 52 on each side of the valve body engages an approximately central opening 54 (the leftmost opening in FIGS. 5 and 7) on the slider unit 44 to releasably hold the slider unit 44 in the open position. By forcing the slider unit 44 toward the barb cap 46 on the valve stem 43 (from right to left in FIG. 5), the walls of the slider unit 44 deflect slightly outwardly such that the approximately central opening 54 disengages from the rib 52 on each side of the valve body 42. The slider unit 44 continues to move in that direction until an opening 54 near the inner end (the right end in FIGS. 5 and 7) of the slider unit 44 passes over, and is engaged by, the rib 52 on each side of the valve body 42.

In this "locked" position, one or more ribs or steps 56 on an upper portion of the slider unit 44 may engage corresponding lower grooves 58 in the button 40 to help maintain the button in the "up" or locked position. Additionally, one or more outwardly projecting ledges 59 may be included on one or both sides of the valve body 42, below the slider unit 44, to inhibit downward movement of the slider unit 44 when the valve is in the locked position.

The spring-loaded retainer 41 includes a cam arm 60 extending over the valve stem 43. When the slider unit 44 is moved from the unlocked to the locked position (from right to left in FIG. 5), a central cover or hood 63 on the slider unit 44 forces the cam arm 60 downwardly such that the face of the free end of the cam arm 60 engages an inward-facing ridge 64 on the valve body 42. In this manner, the retainer 41 and valve stem 43 are prevented from moving into the open position (from left to right in FIG. 5), which significantly minimizes or eliminates leaks in the valve assembly 12. The central hood 63 preferably includes an elevated region 62 for initially accepting the cam arm 60 and guiding the cam arm 60 toward the interior portion of the central hood 63 that downwardly deflects the cam arm 60, Thus, the locking mechanism may include one or more locking devices, including but not limited to the following: ribs 52 on the valve body 42 that engage corresponding openings 54 in the slider unit 44; steps 56 on the slider unit 44 that engage corresponding grooves 58 in the button 40; ledges 59 for maintaining the slider unit 44 in the proper vertical position; and a cam arm 60 on the retainer 41 for engagement with a ridge 64 on the valve body 42. As a result, the valve assembly 12 may be securely and safely held in the locked or closed position, while remaining readily movable between the locked and unlocked positions.

Figure 9:
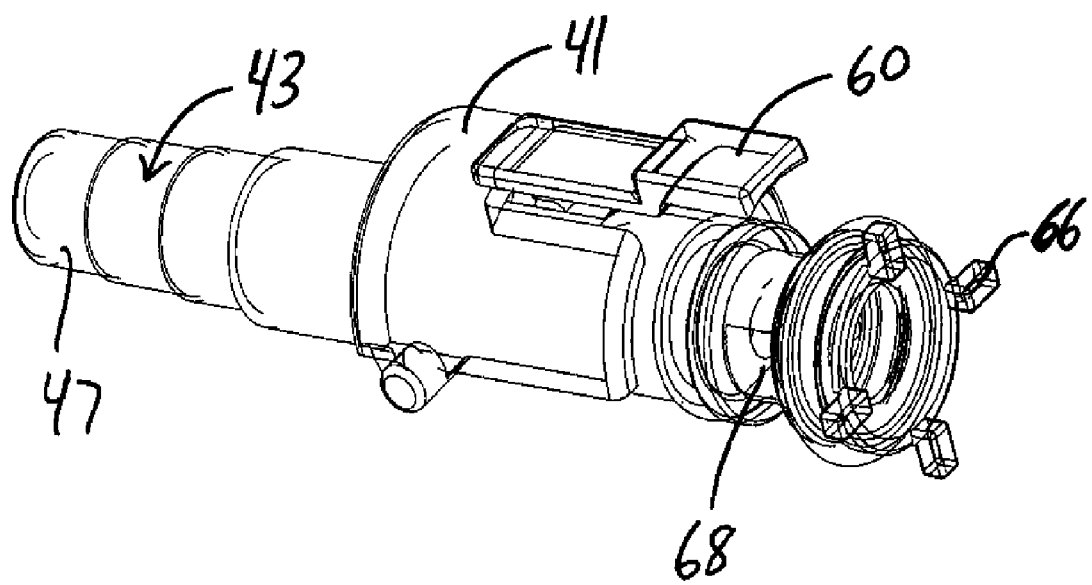
FIG. 9 is a perspective view of the valve stem and cam arm components shown in FIGS. 7 and 8.
Figure 10:
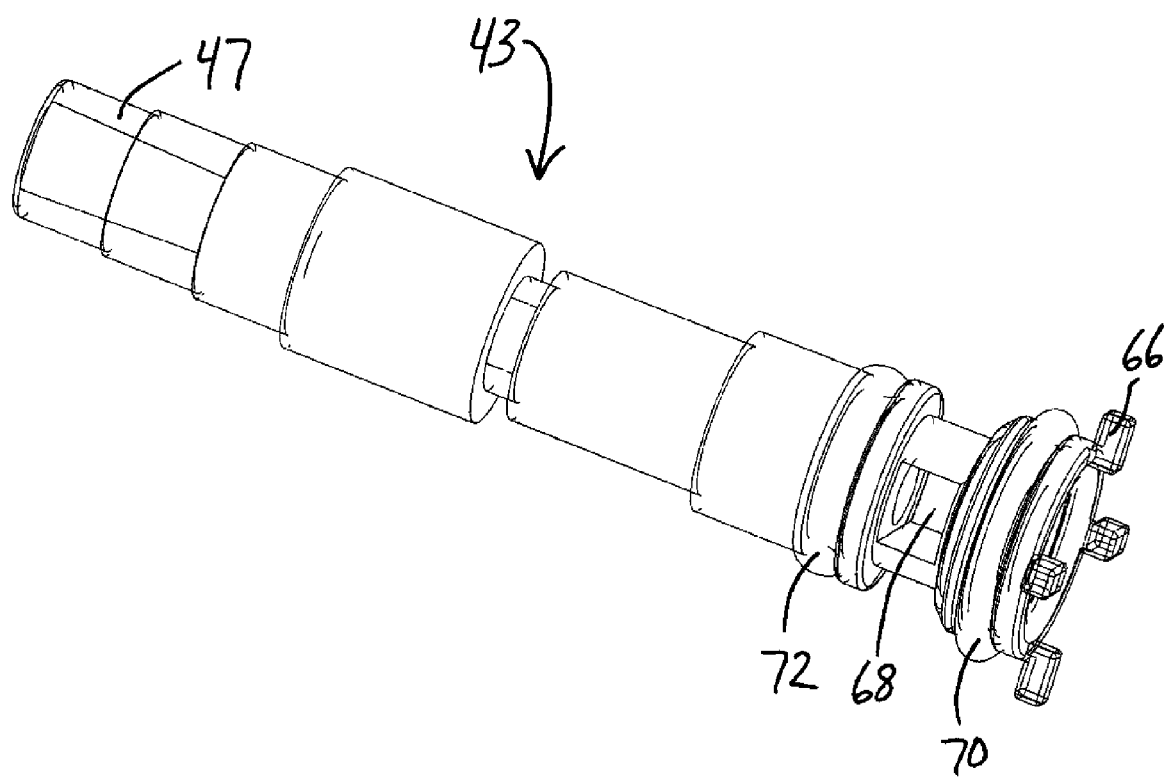
FIG. 10 is a side-perspective view of the valve stem shown in FIGS. 7-9.

Referring to FIGS. 9 and 10, the valve stem 43 preferably includes multiple outwardly projecting legs 66 for centering the valve stem 43 within the valve body 42. The legs 66 are configured to fit closely within the valve body 42 so that the valve stem 43 remains at least substantially straight and aligned (i.e., does not become angled relative to the longitudinal axis of the valve body 42) within the valve body 42. By maintaining the valve stem 43 in proper alignment within the valve body 42, the valve opens smoothly and efficiently when the button 40 is pressed. In many existing systems, the valve stem may readily become misaligned, which may lead to leaking and reduced suction capabilities.

The valve stem 43 includes one or more openings 68 through which air is suctioned when the valve stem 43 is moved into the unlocked or open position. By providing a relatively large opening through the valve stem 43, a large vacuum or suctioning force may be created while producing minimal audible noise. The valve stem 43 preferably includes a first O-ring 70 or other suitable seal on a first side of the opening 68, and a second O-ring 72 or other suitable seal on a second side of the opening 68, for sealing with the interior of the valve body 42.

Referring to FIGS. 11-15, a tube wiper 74 is slidably secured to the catheter tube 13. The tube wiper 74 is positioned within a cleaning shield 77 inside the lavage housing 21. (The cleaning shield 77 is visible in FIG. 15, in which the lavage housing 21 is removed for clarity.) The interior of the lavage housing 21 may include ribs or other guides for funneling fluid though the lavage housing 21, which facilitates more efficient cleaning of the cleaning shield 77. The cleaning shield 77 preferably includes slots 71 formed between legs 73 of the cleaning shield 77. Cleaning fluid injected into the lavage housing 21 passes around the cleaning shield 77, and through the slots 71 in the cleaning shield 77, to clean the catheter tube 13 (including the openings 11 therein), the tube wiper 74, and seals and other components in and around the lavage housing 21.

The catheter tube 13 is longitudinally slidable or movable through an opening 76 in the tube wiper 74 to allow the catheter tube 13 to be inserted into, and withdrawn from, a patient's lungs. A catheter guide 75 (visible in FIGS. 4 and 15) may be located within the inner arm 24 of the manifold 16, in front of the lavage housing 21, to aid in guiding the catheter tube 13 through the manifold 16. The catheter guide 75 preferably includes one or more openings or splits 79 for allowing fluid resting in the manifold 16 to readily travel to the catheter tube 13, when the manifold 16 is rotated, for removal from the system.

The cleaning shield 77, catheter guide 75, and lavage housing 21 preferably include keyways for locking them into place relative to one another. For example, the cleaning shield may include a raised ridge or "key" 81 for engagement with a receiving slot 83 in the catheter guide 75. Similarly, the exterior of the receiving slot 83, or another raised ridge on the catheter guide 75, may act as a key for engagement with a receiving slot in the lavage housing 21. Accordingly, the cleaning shield 77, catheter guide 75, and lavage housing 21 do not rotate relative to one another during cleaning operations, and they do not need to be glued together to prevent such rotation.

The tube wiper 74 may include a substantially circular base ring 78 and a substantially frusto-conical body 80, or it may have any other suitable configuration. The tube wiper 74 includes a leading ridge 82 for "pushing" fluid present on an outer surface of the catheter tube 13 into the lavage housing 21 when the catheter tube 13 is withdrawn from a patient's lungs. Thus, the leading ridge 82 substantially prevents mucus and other fluids from entering the region of the catheter contained within the sheath 14.

The tube wiper 74 may further include multiple ribs 84 for providing structural support to the tube wiper 74. The ribs 84 prevent the leading ridge 82 from collapsing or deforming when the catheter tube 13 is pulled through the tube wiper 74. Thus, the leading ridge 82 is able to maintain its form on the outer surface of the catheter tube 13 and to at least substantially prevent mucus and other fluids from entering the interior of the tube wiper 74.

The tube wiper 74 preferably further includes an internal ledge 86 positioned around its inner circumference. The internal ledge 86 acts to push into the lavage housing 21 any mucus or other fluid that gets past the leading ridge 82. Thus, the internal ledge 86 acts as a secondary wiping mechanism to further prevent mucus or other fluid from entering the portion of the catheter contained within the sheath 14. By including the ribs 84 or the internal ledge 86, the cleaning efficiency of the tube wiper 74 is substantially increased.

Figure 13:
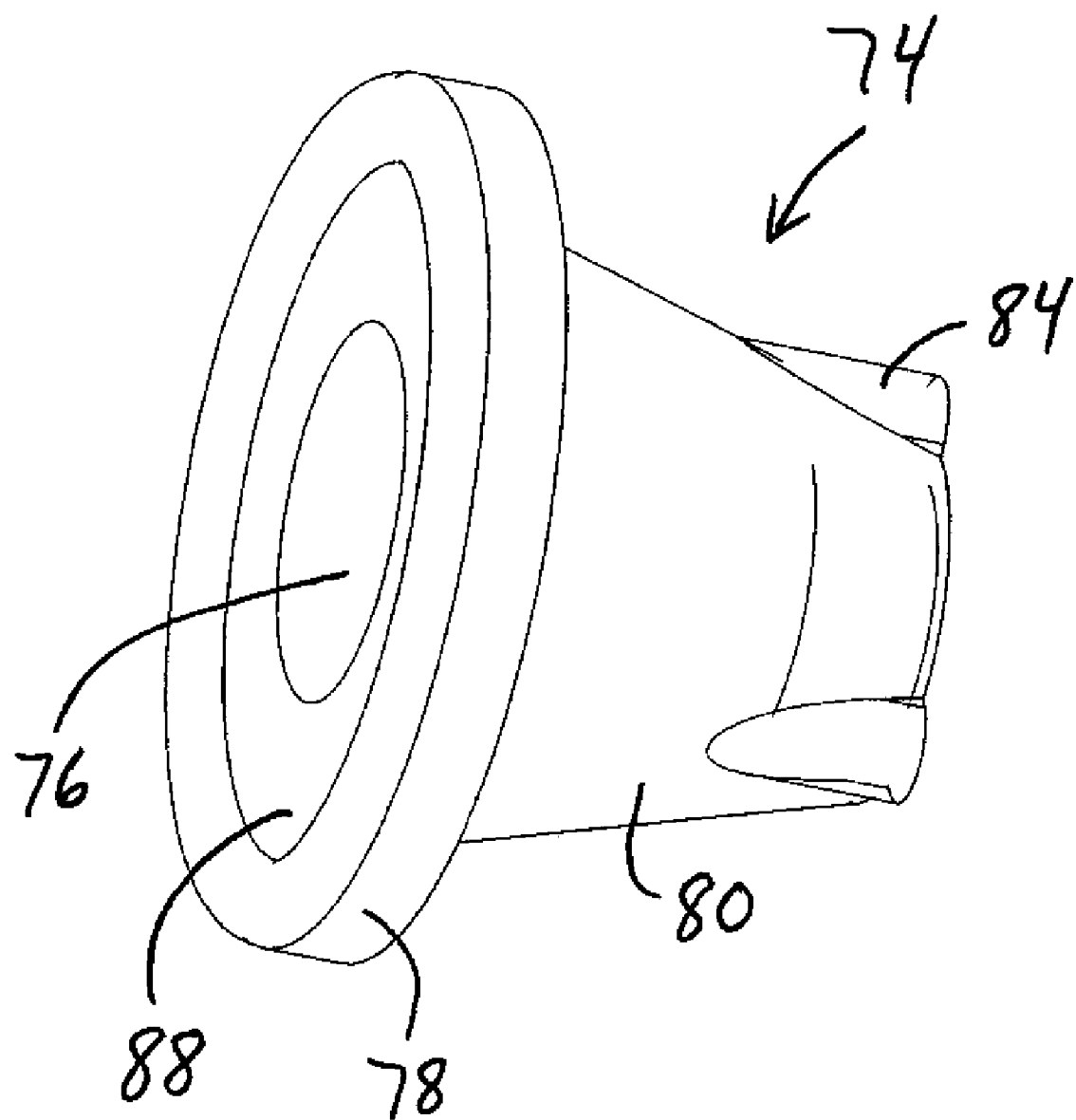
FIG. 13 is a side-perspective view of the tube-wiper shown in FIGS. 11 and 12.
Figure 14:
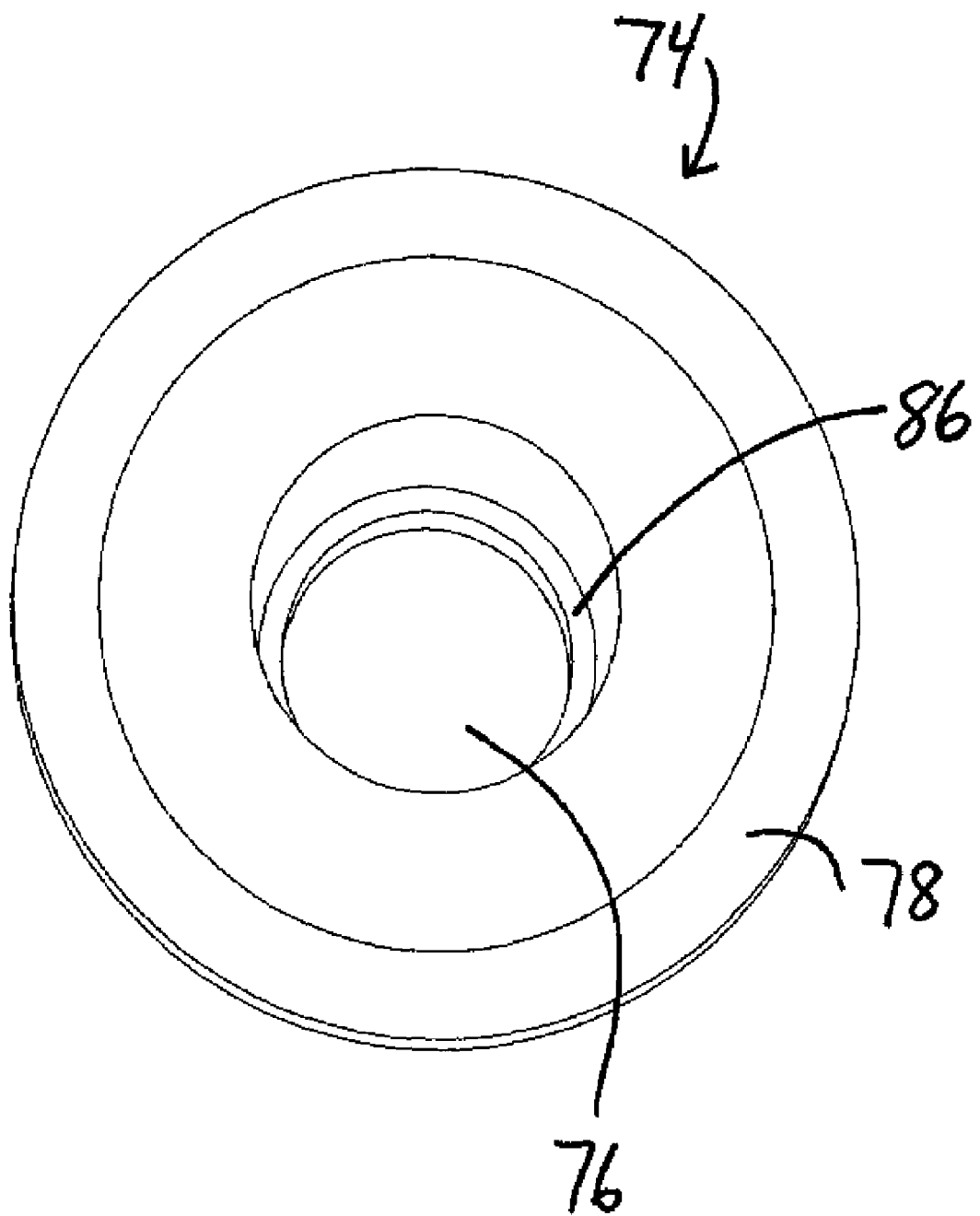
FIG. 14 is a rear-perspective view of the tube-wiper shown in FIGS. 11-13.

As shown in FIGS. 13 and 14, the lower surface of the base ring 78 may extend beyond the internal body 80 of the tube wiper 74. As a result, a recessed portion 88 is formed in the body 80 of the tube wiper 74 for mating with an O-ring or other internal portion of the lavage housing 21. In this manner, the base ring 78 of the tube wiper 74 may seat securely around an O-ring or other internal portion of the lavage housing 21. A washer is preferably included between the upper surface of the base ring 78 and the legs 73 of the cleaning shield 77 for applying even and equal pressure on each of the legs 73 and on the base ring 82. This even pressure causes the tube wiper 74 to efficiently seal with the O-ring (or with the other internal portion of the lavage housing 21) that mates with the recessed portion 88 of the tube wiper 74.

All of the components described herein may be made of a lightweight plastic material or other suitable materials. The various components may be glued to one another via a suitable adhesive, or may be attached via a snap-fit or lock-fit, or may be attached in any other suitable manner. Additionally, the various components of the closed suction catheter 10 may have any suitable weights or dimensions, and the system may be adapted to accommodate catheter tubes of different sizes (e.g., 12 mm-French and 14 mm-French catheter tubes).

In use, the upper arm 20 of the manifold 16, or the flexible tube 18, if used, is connected to or coupled to a tube or hose on a ventilator. The outer arm 19 of the manifold 19 is connected to or coupled to an endotracheal tube or other artificial airway inserted into a patients lungs. The barb portion 47 of the valve stem 43 is connected, via suction tubing or a similar connector, to a vacuum system or other suction system.

When the time comes to remove mucus or other fluids from the patient's lungs, an attendant slides the catheter tube 13 through the outer arm 19 of the manifold 16 so that it travels down through the artificial airway and enters the patient's lungs (the attendant manipulates the catheter tube 13 by pressing the sheath 14 against the outer surface of the catheter tube 13 and then pushing or pulling the tube 13 in the desired direction). If the slider unit 44 on the locking mechanism is in the locked position, the attendant slides the slider unit 44 into the unlocked position and presses the button 40 to open a the valve and create a suctioning force through the openings 11 in the catheter tube 13.

This suctioning force causes mucus and other fluid to flow into (and onto) the catheter tube 13. After pressing and holding the button 40 (one or more times), the attendant withdraws the catheter tube 13 from the patient's lungs by pulling on the catheter tube 13 or on the valve assembly 12. As the catheter tube 13 slides through the tube wiper 74, the leading ridge 82 and the internal ledge 86 on the tube wiper 74 wipe mucus and other fluid from the catheter tube 13 such that the fluid remains in the lavage housing 21 and does not enter the portion of the catheter contained within the sheath 14.

If the catheter tube 13 is inadvertently pulled too far, such that the openings 11 in the catheter tube 13 move beyond the tube wiper 74, the sheath 14 will become filled with air. If this occurs, the attendant can simply slide the catheter tube 13 forward until the openings 11 pass back through the tube wiper 74 and into the lavage housing 21 or manifold. The attendant may then remove excess air from the sheath 14 by squeezing the sheath 14 near the manifold 16 and running his or her fingers along the length of the catheter tube 13 to force the air out through outlet holes in the intake 50.

Once the catheter tube 13 is retracted into the lavage housing 21, the attendant may inject cleaning fluid into the lavage housing 21, via the poppet valve 29 in the valve body 28, to clean the leading end of the catheter tube 13 (including the openings 11 therein), the tube wiper 74, and any seals or other components in the lavage housing 21. The injected cleaning fluid travels through (or around, as described above) the poppet valve 29, along the lavage tube 22, through the lavage elbow 26, into the lavage housing 21, and around, as well as through the slots 71 in, the cleaning shield 77 to clean the system components, including the tube wiper 74.

When the cleaning process is completed, any waste fluid in the manifold 16 may be removed by removing the manifold cap 32 from the lower arm of the manifold 16 and draining out the fluid. Waste fluid may also be removed by rotating the manifold 16 such that the waste fluid travels through the openings or splits 79 in the catheter guide 75 to a location near the openings 11 in the catheter tube 13. The button 40 may then be pressed to suction the fluid into the catheter tube 13.

When the suctioning and cleaning processes are completed, the attendant may slide the slider unit 44 into the locked position so that inadvertent pressing of the button 40 is prevented, and so that the valve stem 43 is held securely in place by the cam arm 60. The suctioning process may be repeated several times before disposal of the catheter 10 is required.

Thus, while several embodiments have been shown and described, various changes and substitutions may of course be made, without departing from the spirit and scope of the invention. For example, many of the method steps described herein may be performed in a different order than that which is explicitly described. Furthermore, while several features and improvements have been described, the invention may include any combination of one or more of those features, and not all of the features are required in every embodiment of the invention. The invention, therefore, should not be limited, except by any claims and their equivalents.

What is claimed is:

1. A suction catheter, comprising:
 a valve assembly;
 a manifold;
 a catheter tube attached to the valve assembly and slidably secured within the manifold; and
 a tube wiper on an exterior surface of the catheter tube, with the tube wiper comprising:
  a wiper body including a leading ridge for wiping the exterior surface of the catheter tube, wherein the leading ridge is reinforced by a plurality of ribs; and
  a ledge on an inner surface of the wiper body for wiping the exterior surface of the catheter tube.

2. The suction catheter of claim 1 wherein the tube wiper further includes a base ring at a lower end of the wiper body.

3. The suction catheter of claim 2 wherein a recess is formed within the base ring for mating with an O-ring.

4. The suction catheter of claim 1 wherein the valve assembly comprises:
 a valve body;
 a valve stem within the valve body;
 a button for actuating the valve stem; and
 a locking mechanism for maintaining the button in a locked position.

5. The suction catheter of claim 4 wherein the locking mechanism comprises:
 a cam arm;
 a slider unit movable along the valve body between a locked position, in which the slider unit deflects the cam arm into engagement with the valve body to prevent movement of the valve stem, and an unlocked position.

6. The suction catheter of claim 5 wherein the locking mechanism further comprises at least one rib on the valve body configured to engage corresponding openings on the slider unit for maintaining the slider unit in the locked and unlocked positions.

7. The suction catheter of claim 1 further comprising a lavage housing connected to the manifold, wherein the tube wiper is contained within the lavage housing.

8. The suction catheter of claim 7 further comprising a cleaning shield secured within the lavage housing and surrounding the wiper body, wherein the cleaning shield includes a plurality of slots for providing a fluid flow path to the wiper body.

9. The suction catheter of claim 7 further comprising a catheter guide in fluid communication with the lavage housing, wherein the catheter guide includes at least one split for providing a fluid flow path from an interior of the manifold to an interior of the catheter guide.

10. The suction catheter of claim 7 further comprising a poppet valve for providing fluid into the lavage housing, wherein the poppet valve includes a plurality of ridges on an outer surface thereof for directing fluid that flows around the poppet valve into the lavage housing.

11. The suction catheter of claim 1 further comprising:
a lavage housing connected to the manifold;
a cleaning shield secured within the lavage housing; and
a catheter guide in fluid communication with the lavage housing;
wherein the lavage housing, the cleaning shield, and the catheter guide are engaged with one another via keyways, such that the lavage housing, the cleaning shield, and the catheter guide do not rotate relative to one another.

12. The suction catheter of claim 1 further comprising a sheath connected to the valve assembly and the manifold and surrounding a portion of the catheter tube located between the valve assembly and the manifold.

13. The suction catheter of claim 1 further comprising a flexible tube rotatably connected to the manifold, wherein the flexible tube is configured for coupling to a ventilator.

14. A suction catheter, comprising:
a manifold;
a catheter tube including a first end movably secured within the manifold; and
a valve assembly attached to a second end of the catheter tube, with the valve assembly comprising:
a valve body;
a valve stem within the valve body;
an actuator for moving the valve stem; and
a locking mechanism for maintaining the actuator in a locked position, wherein the locking mechanism comprises:
a cam arm;
a slider unit movable along the valve body between a locked position, in which the slider unit forces the cam arm into engagement with the valve body to prevent movement of the valve stem, and an unlocked position.

15. The suction catheter of claim 14 wherein the slider unit includes at least one step on an upper surface thereof configured to engage a corresponding groove in the actuator for maintaining the actuator in the locked position.

16. The suction catheter of claim 14 wherein the valve body includes at least one outwardly projecting rib configured to engage corresponding openings on the slider unit for maintaining the slider unit in the locked and unlocked positions.

17. The suction catheter of claim 14 wherein the valve body includes at least one outwardly projecting ledge located below the slider unit to inhibit downward movement of the slider unit when the locking mechanism is in the locked position.

18. The suction catheter of claim 14 wherein the valve stem includes a barb portion for connection with a suction source.

19. The suction catheter of claim 14 further comprising an intake on the catheter tube including an outlet port and an exit port for releasing air, with the exit port oriented at approximately 90° to the outlet port.

20. A suction catheter, comprising:
valve means for providing suctioning force through the catheter;
a manifold;
a catheter tube attached to the valve means and movably secured within the manifold;
a tube wiper on an exterior surface of the catheter tube, with the tube wiper comprising:
primary wiping means located on an exterior of the tube wiper for wiping the exterior surface of the catheter tube; and
secondary wiping means protruding radially inwardly relative to the primary wiping means from an interior surface of the tube wiper for wiping the exterior surface of the catheter tube.

21. The suction catheter of claim 20 further comprising reinforcing means on the primary wiping means for providing structural support to the primary wiping means.

22. A suction catheter, comprising:
a valve assembly;
a manifold;
a catheter tube attached to the valve assembly and slidably secured within the manifold;
a tube wiper on an exterior surface of the catheter tube, including an external primary wiper and an internal secondary wiper;
wherein the valve assembly comprises:
a valve body;
a valve stem within the valve body; and
a locking mechanism comprising:
a cam arm;
a slider unit movable along the valve body between a locked position, in which the slider unit forces the cam arm into engagement with the valve body to prevent movement of the valve stem, and an unlocked position.

* * * * *